United States Patent
Jin et al.

(10) Patent No.: US 10,610,173 B2
(45) Date of Patent: Apr. 7, 2020

(54) SYSTEM AND METHOD TO IMPROVE SPATIAL RESOLUTION IN COMPUTED TOMOGRAPHY

(71) Applicant: General Electric Company, Schenectady, NY (US)

(72) Inventors: Yannan Jin, Niskayuna, NY (US); Jiahua Fan, New Berlin, WI (US); Mingye Wu, Glenville, NY (US); Feng Chen, Niskayuna, NY (US); Bruno Kristiaan Bernard De Man, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 304 days.

(21) Appl. No.: 15/872,169

(22) Filed: Jan. 16, 2018

(65) Prior Publication Data
US 2019/0216413 A1    Jul. 18, 2019

(51) Int. Cl.
*A61B 6/00* (2006.01)
*H01J 35/00* (2006.01)
*A61B 6/03* (2006.01)

(52) U.S. Cl.
CPC ............ *A61B 6/405* (2013.01); *A61B 6/032* (2013.01); *A61B 6/4021* (2013.01); *A61B 6/4208* (2013.01); *A61B 6/4435* (2013.01); *A61B 6/482* (2013.01)

(58) Field of Classification Search
CPC ............ H01J 2235/086; H01J 2235/00; H01J 2235/10; H01J 35/00; H01J 35/14; H01J 35/02; G01N 23/04
See application file for complete search history.

(56) References Cited

U.S. PATENT DOCUMENTS

| 7,268,814 | B1 | 9/2007 | Pain et al. |
| 7,675,561 | B2 | 3/2010 | Lepage |
| 7,792,241 | B2 | 9/2010 | Wu et al. |
| 7,826,587 | B1 | 11/2010 | Langan et al. |
| 7,929,659 | B2 | 4/2011 | Dong et al. |
| 2012/0163530 | A1* | 6/2012 | Sainath ............... A61B 6/027 378/5 |
| 2014/0177794 | A1 | 6/2014 | De et al. |
| 2014/0177808 | A1 | 6/2014 | Charette et al. |
| 2014/0185741 | A1 | 7/2014 | Shen et al. |
| 2015/0178958 | A1 | 6/2015 | Zou |
| 2016/0166221 | A1 | 6/2016 | Gao et al. |

(Continued)

OTHER PUBLICATIONS

Tesic et al., "Full Field Digital Mammography Scanner", European Journal of Radiology, http://www.sciencedirect.com/science/article/pii/S0720048X99000649, vol. 31, Issue 01, pp. 2-17, Jul. 1999.

(Continued)

*Primary Examiner* — Don K Wong

(57) ABSTRACT

The present approach relates to avoiding azimuthal blur in a computed tomography context, such as in dual energy imaging with fast kV switching. In accordance with certain aspects, the focal spot position is held stationary in the patient coordinate system within each respective view and the detector signals within the view are summed. In one embodiment, this results in the low and high energy views within the signal being collected from the same position within the patient coordinate system.

20 Claims, 9 Drawing Sheets

(56) References Cited

U.S. PATENT DOCUMENTS

2017/0000437 A1     1/2017   Zhang et al.
2017/0065240 A1     3/2017   Zou et al.

OTHER PUBLICATIONS

Flohr et al., "Image Reconstruction and Image Quality Evaluation for a 64-Slice CT Scanner with Z-Flying Focal Spot.", Medical Physics, https://www.ncbi.nlm.nih.gov/pubmed/16193784, vol. 32, Issue 08, pp. 36-47, Aug. 2005.
Kachelriess et al., "Flying Focal Spot (FFS) in Cone-Beam CT", IEEE Transactions on Nuclear Science, http://ieeexplore.ieee.org/document/1645021/, vol. 53, Issue 03, pp. 1238-1247, Jun. 2006.
Nowak et al., "Time-Delayed Summation as a Means of Improving Resolution on Fast Rotating Computed Tomography Systems.", Medical Physics, https://www.ncbi.nlm.nih.gov/pubmed/22482646, vol. 39, Issue 04, pp. 49-60, Apr. 2012.
Baojun Li, "Dual-Energy CT with Fast-kVp Switching and Its Applications in Orthopedics", OMICS Journal of Radiology, https://www.omicsonline.org/open-access/dualenergy-ct-with-fastkvp-switching-and-its-applications-in-orthopedics-2167-7964.1000137.php?aid=16736, Aug. 1, 2013.
Duan et al., "The Influence of Tube Current on X-Ray Focal Spot Size for 70 KV CT Imaging", AAPM 56th Annual Meeting & Exhibition, http://www.aapm.org/meetings/2014am/PRAbs.asp?mid=90&aid=23261, Jul. 20-24, 2014.
Chang et al., "The Focal Spot Model Based High Spatial Resolution Iterative Reconstruction Method for a Dual-Focus CT", Nuclear Science Symposium and Medical Imaging Conference, http://ieeexplore.ieee.org/document/7430890/, Nov. 8-15, 2014.

\* cited by examiner

| VIEW  | VIEW-1      |             |             | VIEW-2      |             |             | VIEW-3      |             |             |
|-------|-------------|-------------|-------------|-------------|-------------|-------------|-------------|-------------|-------------|
| $P_1$ | $N_{1,1,1}$ | $N_{1,1,2}$ | $N_{1,1,3}$ | $N_{1,2,1}$ | $N_{1,2,2}$ | $N_{1,2,3}$ | $N_{1,3,1}$ | $N_{1,3,2}$ | $N_{1,3,3}$ |
| $P_2$ | $N_{2,1,1}$ | $N_{2,1,2}$ | $N_{2,1,3}$ | $N_{2,2,1}$ | $N_{2,2,2}$ | $N_{2,2,3}$ | $N_{2,3,1}$ | $N_{2,3,2}$ | $N_{2,3,3}$ |
| $P_3$ | $N_{3,1,1}$ | $N_{3,1,2}$ | $N_{3,1,3}$ | $N_{3,2,1}$ | $N_{3,2,2}$ | $N_{3,2,3}$ | $N_{3,3,1}$ | $N_{3,3,2}$ | $N_{3,3,3}$ |

FIG. 7

SYSTEM AND METHOD TO IMPROVE SPATIAL RESOLUTION IN COMPUTED TOMOGRAPHY

BACKGROUND

The subject matter disclosed herein relates to dual-energy X-ray imaging.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray-based imaging technologies, X-ray radiation spans a subject of interest, such as a human patient, and a portion of the radiation impacts a detector where the intensity data is collected. In scintillator-based detector systems, a scintillator material generates optical or other low-energy photons when exposed to the X-ray and a photodetector then produces signals representative of the amount or intensity of radiation observed on that portion of the detector. The signals may then be processed to generate an image that may be displayed for review. In CT systems, this X-ray transmission information is collected at various angular positions as a gantry is rotated around a patient to allow volumetric reconstructions to be generated.

In clinical practice it may be desirable to acquire such X-ray transmission data at more than one X-ray energy, or spectrum, as the difference in X-ray transmission at the different energies can be leveraged to generate images corresponding to different tissue types or conveying information related to the spatial material composition within the imaged region. Such approaches, in a computed tomography context, may be characterized as spectral CT, dual-energy CT or multi-energy CT.

As discussed herein, the spectra may be characterized by the maximum operating voltage (kVp) of an X-ray tube used to generate the X-rays, also denoted as the operating voltage level of the X-ray tube. Though such X-ray emissions may be generally described or discussed herein as being at a particular energy level (e.g., referring to the electron beam energy level in a tube with an operating voltage of, for example, 70 kVp, 150 kVp, and so forth), the respective X-ray emissions actually comprise a continuum or spectrum of energies and may, therefore, constitute a polychromatic emission centered at, terminating at, or having a peak strength at, the target energy.

Such multi-energy imaging approaches necessitate being able to separate the signal attributable to different energy spectra or to different regions of a single spectrum, i.e., good energy separation. Current approaches to achieve energy separation all have drawbacks or tradeoffs related to poor separation of the different energy levels or poor synchronicity, i.e., a temporal offset between when corresponding signals for different spectra are acquired, and/or poor radial correspondence or spatial resolution, i.e., the different energy signals may be acquired at radially offset positions from one another using separate emission and/or detection components.

For example, in a "fast kV switching" dual-energy CT context, an X-ray source (e.g., X-ray tube) is rapidly switched between two or more operating voltages (each of which is associated with a different respective X-ray energy spectrum) at each view angle during gantry rotation. Although the projection data at different energy levels are collected consecutively within two views (which may be preferable than a rotate-rotate or dual source scheme in terms of the temporal offset between different energies) the fast kV switching approach still requires interpolation for view registration. This results in azimuthal blur that may limit improvements in spatial resolution.

BRIEF DESCRIPTION

In one aspect of the present approach, a method for acquiring computed tomography data is provided. In accordance with this embodiment, an X-ray source and detector are continuously rotated about an imaging volume during an examination. The rotation of the X-ray source and detector is through a plurality of discrete view positions. At each view position: the focus of a beam of electrons on a target of the X-ray source is adjusted so that a focal spot on the target remains relatively stationary relative to the imaging volume while in a respective view position; and detector signals acquired over a plurality of pixels are summed while in the respective view position. The summed detector signals acquired at each view are processed to reconstruct an image.

In a further aspect of the present approach, a computed tomography (CT) imaging system is provided. In accordance with this aspect, the CT imaging system a memory encoding processor-executable routines for holding a focal spot stationary and summing detector signal within each of a plurality of discrete view positions and a processing component configured to access the memory and execute the processor-executable routines. The routines, when executed by the processing component, cause the processing component to: continuously rotate an X-ray source and detector of the CT imaging system about an imaging volume during an examination, wherein the rotation of the X-ray source and detector is through the plurality of discrete view positions; at each view position: adjust the focus of a beam of electrons on a target of the X-ray source so that a focal spot on the target remains relatively stationary relative to the imaging volume while in a respective view position, and sum detector signals acquired over a plurality of pixels while in the respective view position; and process the summed detector signals acquired at each view to reconstruct an image.

In an additional aspect of the present approach, one or more non-transitory computer-readable media encoding processor-executable routines are provided. In accordance with this aspect, the routines, when executed by a processor, cause acts to be performed comprising: continuously rotating an X-ray source and detector about an imaging volume during an examination, wherein the rotation of the X-ray source and detector is through a plurality of discrete view positions; at each view position: adjusting the focus of a beam of electrons on a target of the X-ray source so that a focal spot on the target remains relatively stationary relative to the imaging volume while in a respective view position, and summing detector signals acquired over a plurality of pixels while in the respective view position; processing the summed detector signals acquired at each view to reconstruct an image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 7 depicts a view and pixel information in accordance with aspects of the present disclosure;

DETAILED DESCRIPTION

Figure 1:
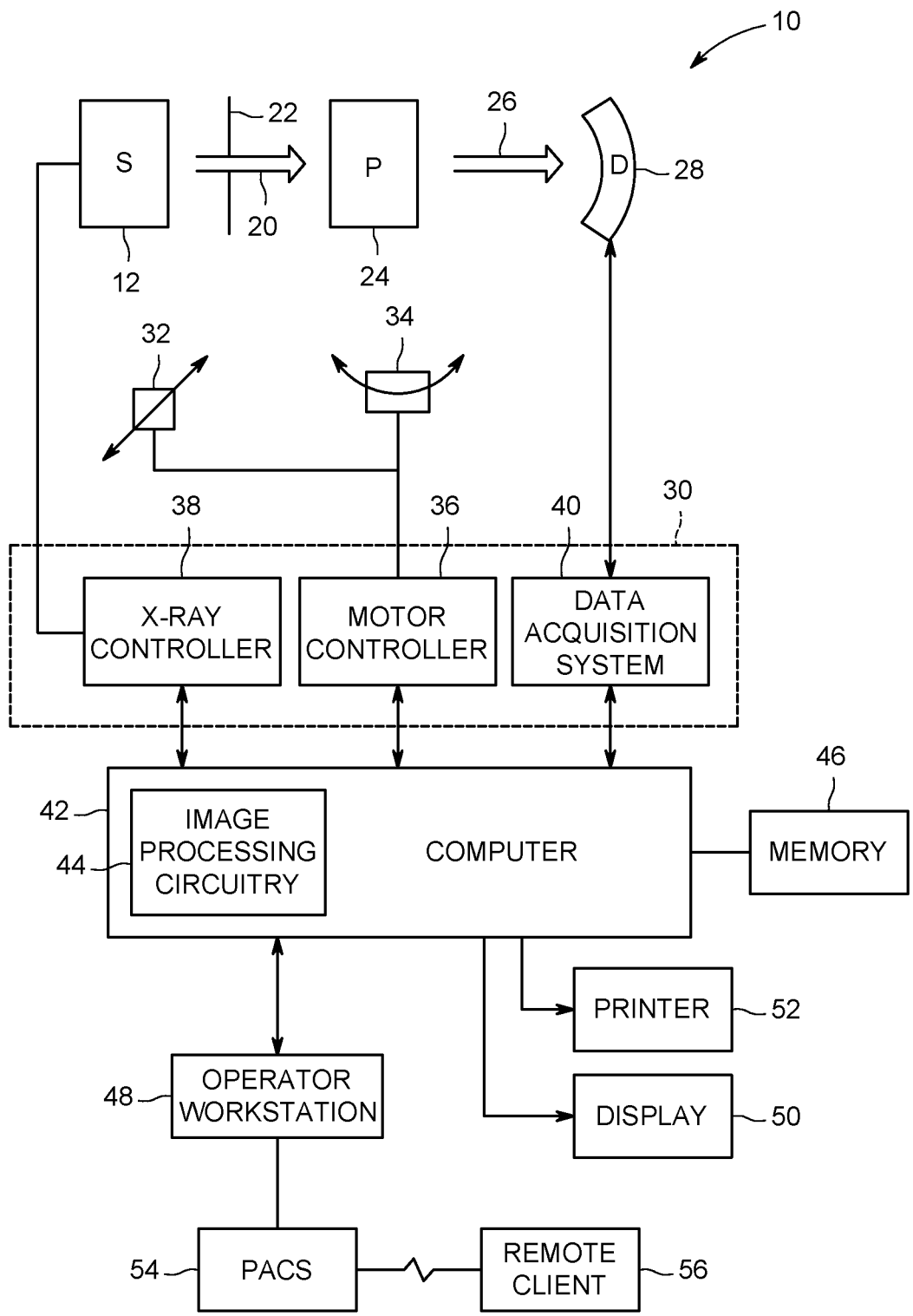
FIG. 1 is a schematic illustration of an embodiment of a computed tomography (CT) system configured to acquire CT images of a patient in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which dual- or multi-energy imaging is desirable, such as spectral computed tomography (CT).

Tissue characterization or classification may be desirable in various clinical contexts to assess the tissue being characterized for pathological conditions and/or to assess the tissue for the presence of various elements, chemicals or molecules of interest. Such approaches may involve use of dual-energy imaging in which data is acquired at a high-energy spectrum and a low-energy spectrum, i.e., two spectra having different mean keV's.

In a fast-kV switching approach to dual-energy imaging, an X-ray source is rapidly switched between high- and low-energy X-ray emissions as it rotates about an imaged volume so as to allow different energy signals to be generated in alternation during rotation of the source.

Although the projection data at different energy levels are collected consecutively within two consecutive views, interpolation is still employed for view registration in conventional approaches, causing azimuthal blur that may limit improvements in spatial resolution. This issue may become more prominent for CT systems with small-pitch (i.e., high-resolution) detectors.

Prior to discussing the present approach for addressing azimuthal blur that may be present in kV switched systems, it may be useful to understand the operation and components of an imaging system that may be used to implement the present approach. With this in mind, FIG. 1 illustrates an embodiment of an imaging system 10 for acquiring dual-energy image data in accordance with aspects of the present disclosure. In the illustrated embodiment, system 10 is a computed tomography (CT) system designed to acquire X-ray projection data at multiple energy spectra, to reconstruct the projection data into volumetric reconstructions, and to process the image data, including material decomposition or tissue-type image data, for display and analysis. The CT imaging system 10 includes an X-ray source 12, such as an X-ray tube, which allows X-ray generation at multiple (e.g., two) spectra having different energy characteristics, during the course of an imaging session. For example, the emission spectra may differ in one or more of their mean, median, mode, maximum, or minimum X-ray energies.

By way of example, in one embodiment an X-ray source 12 (e.g., an X-ray tube) may be switched between a relatively low-energy polychromatic emission spectrum (e.g., X-ray tube operating voltage at about 70 or 80 kVp) and a relatively high-energy polychromatic emission spectrum (e.g., at about 140 or 150 kVp). As will be appreciated, the X-ray source 12 may emit at polychromatic spectra localized around energy levels (i.e., spectra induced by specific kVp ranges) other than those listed herein. Indeed, selection of the respective energy levels for emission may be based, at least in part, on the anatomy being imaged and the chemical or molecules of interest for tissue characterization.

In certain implementations, the source 12 may be positioned proximate to a beam shaper 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements (e.g., a one-dimensional or two-dimensional detector array). Each detector element produces an electrical signal that represents the intensity of the X-ray beam incident at the position of the detector element when the beam strikes the detector 28. Electrical signals from the detector 28 are acquired and processed to generate respective high- and low-energy scan datasets.

Figure 2:
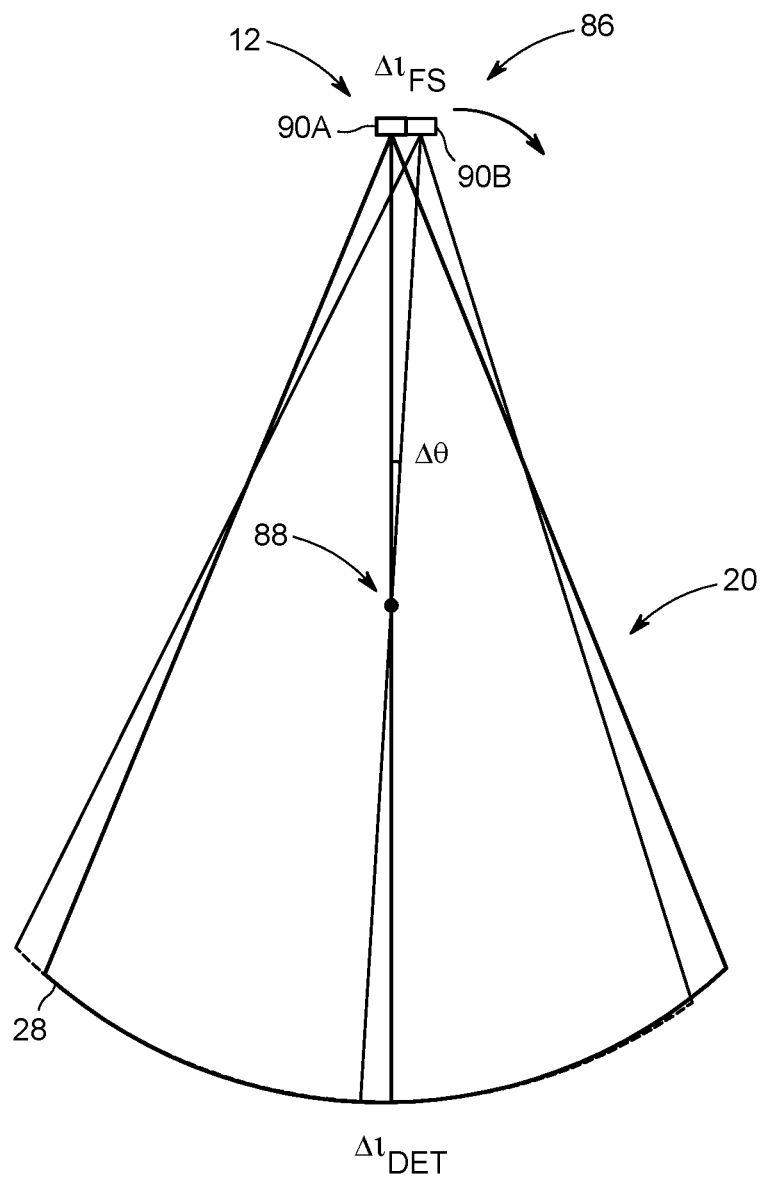
FIG. 2 depicts geometric aspects of source and detector geometry in accordance with aspects of the present disclosure.

To facilitate discussion of the operation and relationships of the detector 28 and source 12 in the techniques described below, a brief discussion of source and detector geometric examples is provided here, with reference to FIG. 2. In particular, FIG. 2 depicts a various geometric concepts and relationships that may be useful in understanding the approaches discussed herein. FIG. 2 schematically depicts a simplified source 12 and detector 28 geometry as they may appear when viewed down the bore of a CT scanner. The source 12 and detector 28 are attached to and rotate with a gantry in accordance with a given examination protocol, as illustrated by rotational arrow 86. With this in mind, the detector 28 and source 12 are illustrated at a first position and a second rotated position. An iso-center 88 is also depicted, which is conventionally understood to correspond to the axis of rotation of the gantry and may also be the geometric position through which the central X-ray of the X-ray beam fan or cone passes.

A focal spot 90 of the X-ray source 12 is illustrated at a first position (focal spot 90A) and a second, rotated position (focal spot 90B). Likewise, the detector 28 is illustrated having similarly been rotated between the corresponding first position and second position. The change in the focal spot position associated with the source 12 between the first and second position may be denoted $\Delta l_{FS}$ while the corresponding change in detector position may be denoted $\Delta l_{Det}$. The corresponding change in angular position between rays passing through the iso-center 88 at the first and second position may be denoted as $\Delta\theta$. Conventionally, the rotation of the source 12 and detector 28, though rotating in a continuous motion, is characterized as being between a number of discrete views or view positions that may be characteristic of the scan system or examination protocol. Other geometric properties of interest may include the source-to-detector distance (SDD) and the source-to-iso-center distance (SID).

With the preceding geometric source and detector principles in mind, and returning to FIG. 1, a system controller 30 commands operation of the imaging system 10 to execute examination protocols and to pre-process or process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and detector 28, such as to generate and/or acquire X-ray transmission data at two or more energy levels or bins, as well as to process the data acquired by the detector 28. In one embodiment, the system controller 30 may be implemented as all or part of a processor-based system such as a general-purpose or application-specific computer system.

The switched X-ray source 12 may be controlled by an X-ray controller 38 contained within the system controller 30. The X-ray controller 38 may be configured to provide power and timing signals to the source 12. As discussed herein, in certain implementations discussed herein, the X-ray controller 38 and/or the source 12 may be configured to provide fast-switching (i.e., near-instantaneous or view-to-view switching) of an X-ray source 12 between two (or more) energy levels. In this manner, the X-ray emissions may be rapidly switched between different kV's at which the source 12 is operated to emit X-rays at different respective polychromatic energy spectra in succession or alternation during an image acquisition session. For example, in a dual-energy imaging context, the X-ray controller 38 may operate an X-ray source 12 so that the X-ray source 12 successively emits X-rays at different polychromatic energy spectra of interest, such that adjacent projections are acquired at different energies (i.e., a first projection is acquired at low-energy, a second projection is acquired at high-energy, and so forth).

The system controller 30 may include a data acquisition system (DAS) 40. The DAS 40 receives data collected by readout electronics of the detector 28, such as sampled digital or analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40.

In the depicted example, the computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation. The memory 46 stores sets of instructions that, when executed by the processor 44, perform image acquisition and/or processing.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote client 56, radiology department information system (RIS), hospital information system (HIS) or to an internal or external network, so that others at different locations can gain access to the image data.

As noted above, the X-ray source 12 may be configured to emit X-rays at multiple energy spectra (e.g., dual-energy). Though such X-ray emissions may be generally described or discussed as being at a particular energy level (e.g., referring to the electron beam energy in a tube with an operating voltage typically in the range of about 70 kVp to about 150 kVp, the respective X-ray emissions actually comprise a continuum or spectrum of energies and may, therefore, constitute a polychromatic emission centered at, terminating at, or having a peak strength at, the target energy. Such differing emission spectra allow attenuation data to be obtained for the same anatomical regions at the different spectra, thereby allowing differential attenuation at the different spectra to be determined for a given tissue or composition. Based on this differential attenuation at the known spectra, material and/or tissue decomposition techniques may be applied.

As noted above, in a kV switching approach to dual-energy imaging using a system such as is shown in FIG. 1, the X-ray source 12 is rapidly switched between high- and low-energy X-ray emissions as it rotates about the imaged volume so as to allow different energy signals to be generated in alternation during rotation of the source 12. Conventional approaches may employ interpolation for view registration, causing azimuthal blur that may limit improvements in spatial resolution.

Figure 3:
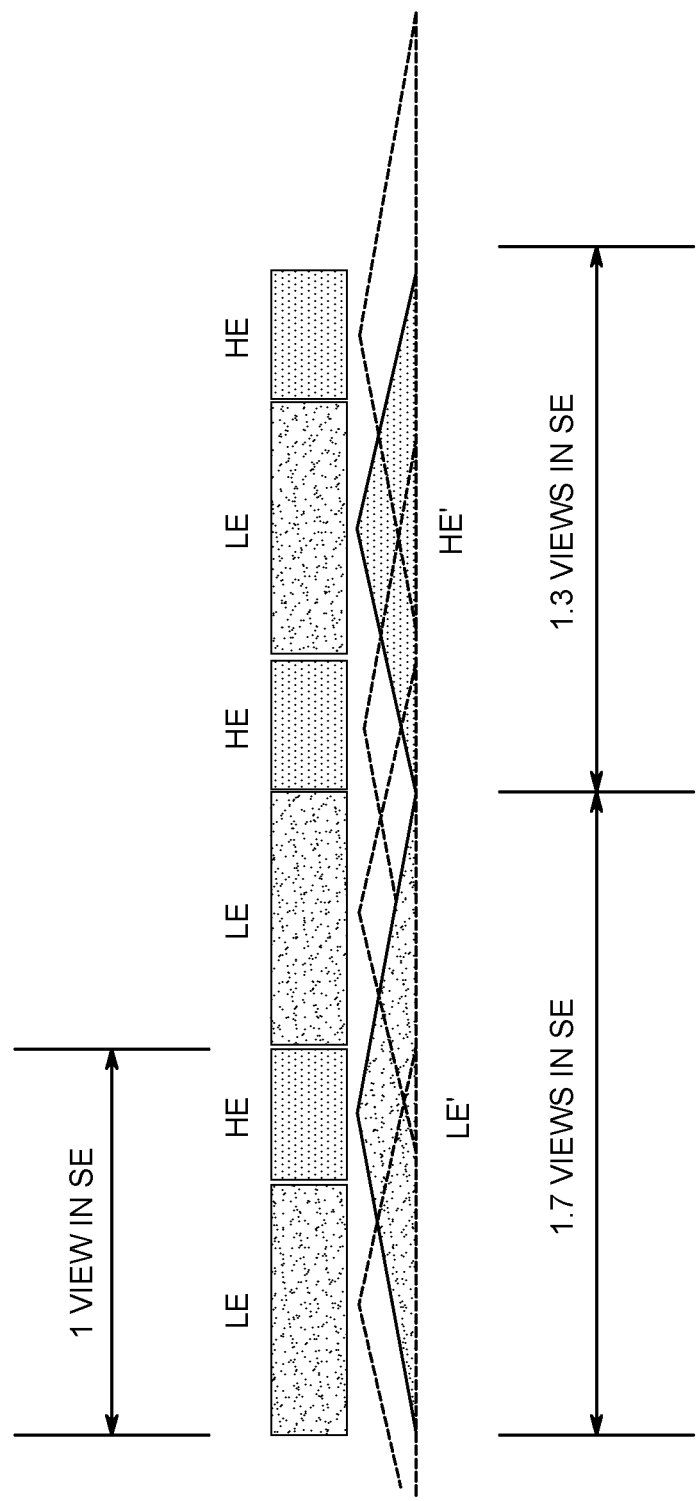
FIG. 3 depicts the impact of view interpolation on spatial resolution in a fast-switching, dual-energy implementation.

The impact on spatial resolution of this view interpolation approach in fast kV switching is illustrated in FIG. 3, which depicts low-energy (LE), high-energy (HE), and single-energy (SE) exposure windows. The x-axis is the time for collecting data at a given view.

This example, for reference, depicts a single energy exposure corresponding to a single view (i.e., each view position is associated with one exposure at the single energy). With respect to illustrating a dual-energy exposure, the view time associated with a conventional SE exposure is divided into alternating LE and HE exposures. That is, the time taken to image a view at a single energy is instead used to perform two exposure events, LE and HE exposures, in duel-energy imaging. View interpolation is performed to generate LE' and HE' interpolations, which are registered to respective LE and HE exposures. In particular, LE' is a synthesized low-energy view derived by interpolating from two neighboring low-energy views. Correspondingly, HE' is a synthesized high-energy view derived by interpolating from two neighboring high-energy views. When the duty ratio of LE/HE is 70%:30% (as shown), which is a typical setting in practice, the LE' and HE' interpolations respectively cover a rotation range equivalent to 1.7 and 1.3 views in single energy, making the azimuthal blur much worse than the single energy case.

To address this azimuthal blur in dual energy imaging with fast kV switching, the present approach freezes the focal spot position and properly sums the detector signals. These steps result in the low and high energy views being collected from the same position, thereby eliminating the interpolation/up-sampling step and improving the spatial resolution. With this in mind, in this dual-energy context a view position as used herein is the discrete position corresponding to a pair of registered low- and high-energy acquisitions.

With respect to focal spot freezing, this technique adjusts the focal spot of the electron beam on the rotating target within the source 12 by adjusting the electric/magnetic field within the X-ray tube so that the electron beam moves relative to the target to compensate for the gantry rotation. This is in contrast to conventional X-ray generation in CT in which the focal spot moves with the gantry rotation within one view, which causes azimuthal blur. The view interpolation conventionally employed in fast kV switching further increases this blur.

Figure 4:
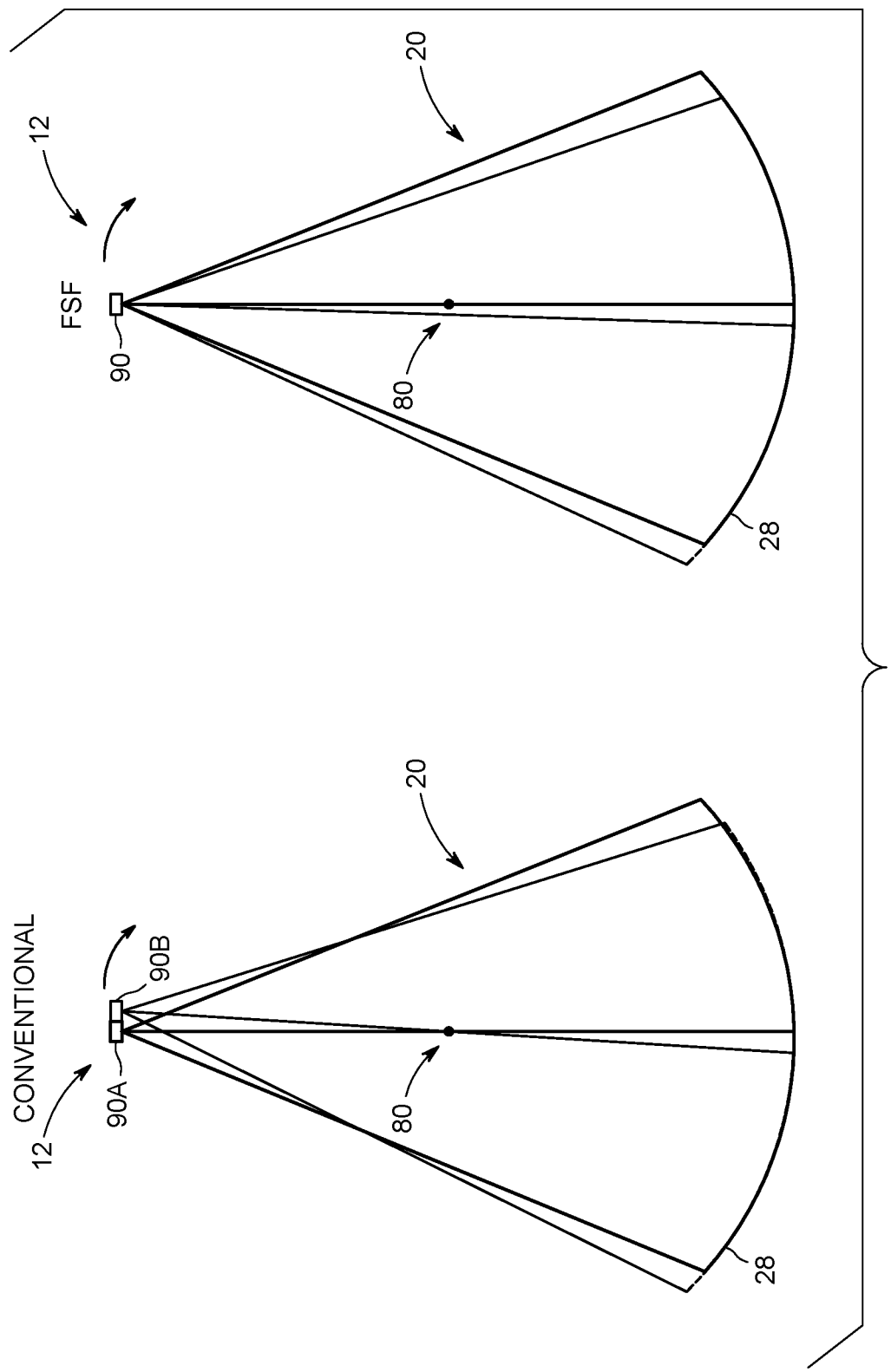
FIG. 4 depicts a side-by-side comparison of conventional (left) and focal-spot-freezing (right) X-ray generation, in accordance with aspects of the present disclosure.

The conventional (left) and focal spot freezing (FSF) (right) approaches are shown in side-by side comparison in FIG. 4. As illustrated in FIG. 4, in both the conventional and FSF examples the gantry moves clock-wise from a first position to a second position within one view. In the conventional approach example, a first focal spot 90A at a first exposure time is shown along with a second focal spot 90B at a second exposure time. As shown, the second focal spot 90B is rotationally offset from the first focal spot 90A due to rotation of the gantry holding the source 12 and detector 28. Thus, in the conventional approach, the focal spot 90 moves continuously, including within a given view, relative to the patient coordinate system.

Conversely, in the focal spot freezing example on the right, the focal spot 90 remains stationary (i.e., 'freezes') in the absolute coordinate system within each respective view (i.e., until the next view). That is, the focal spot 90 is fixed in the patient coordinate system for a respective view until it is time to move to the next view, such that the focal spot 90, though rotated for each view about the imaged volume, is fixed within the respective views so that exposures acquired within a given view are acquired from the same rotational position in the view.

Figure 5:
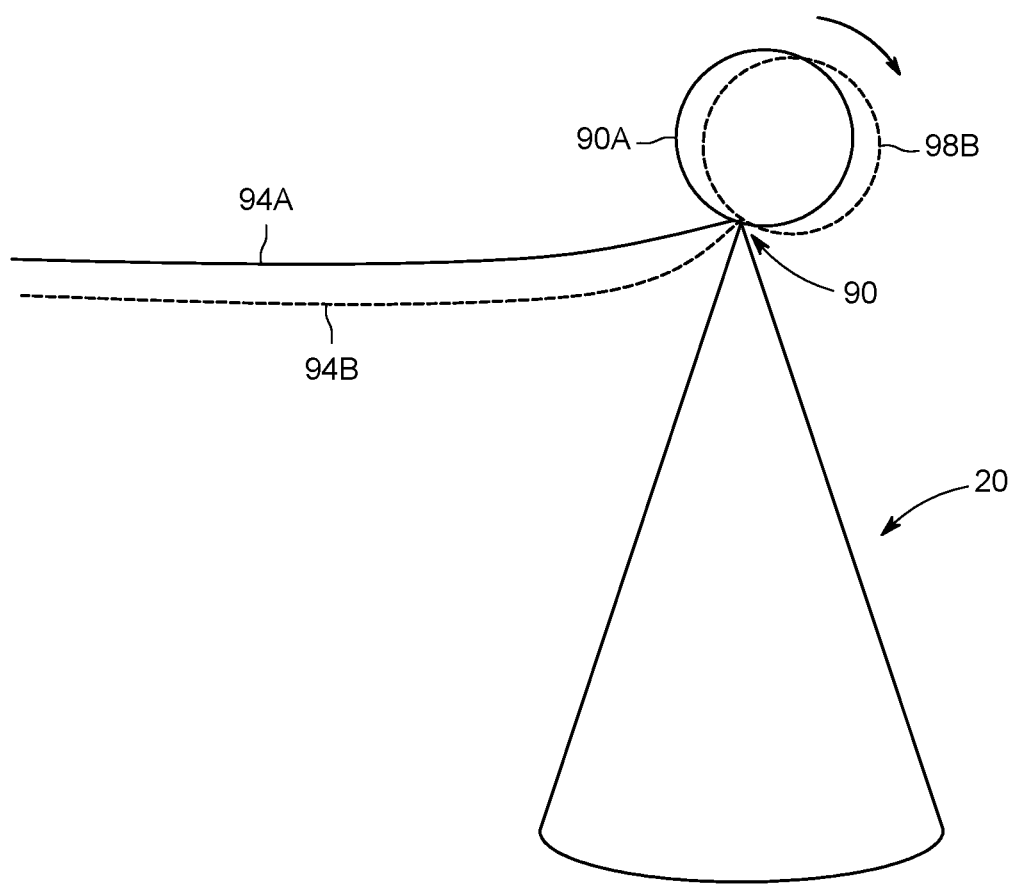
FIG. 5 depicts aspects of electron beam focus adjustment to implement focal spot freezing in accordance with aspects of the present disclosure.

Freezing of the focal spot 90 is achieved by adjusting the electron beam 94 from the cathode, as shown in FIG. 5. As shown in FIG. 5, the target 98 rotates from a first position (target 98A) to a second position (target 98B) within a view position during an exposure. The focal spot 90 is the point at which the electron beam 94 impacts the target 98 and from which X-rays 20 are generated and emitted. As shown in this example, the focusing of the electron beam 94 is adjusted as the target 98 moves within the view position (i.e., from the path of electron beam 94A impacting target 98A to the path of electron beam 94B impacting target 98B). The refocusing of the electron beam may be accomplished using the electric/magnetic fields that are present to steer the electron beam 94 toward the target 98. As a consequence of the adjustment to the electron beam path, the focal spot 90 remains relatively stationary despite the target 98 having moved within the view position. When the target 98 reaches the next view position as the gantry rotates, the electron beam 94 is refocused on the initial focal spot position for a view position (e.g., electron beam path 94A) and the focus adjustment is repeated in the new view position. In this manner, as the X-ray source 12 rotates from view position to view position about the imaged volume, the focal spot 90 at each view position is held relatively fixed (i.e., frozen) relative to the imaged volume until the next view position is reached.

While the preceding relates the use of the focal spot freezing approach to maintain a fixed focal spot 90 within each view, this technique is not enough alone to freeze a respective view because the detector 28 is also rotating along with the gantry within each view. To address this motion embodiments of the present approach may employ a detector signal summation technique to combine the detector signal during the gantry rotation. In particular, a digital signal summation implementation in conjunction with focal spot freezing can freeze the entire view. In this manner, detector signal summation may be employed such that the signal sampled by a detector pixel within a respective view is properly combined to eliminate the azimuthal blur in the measure view. Further, in a dual energy context as described herein, the low-energy and high-energy signals can be precisely aligned, without need of up-sampling.

Figure 6:
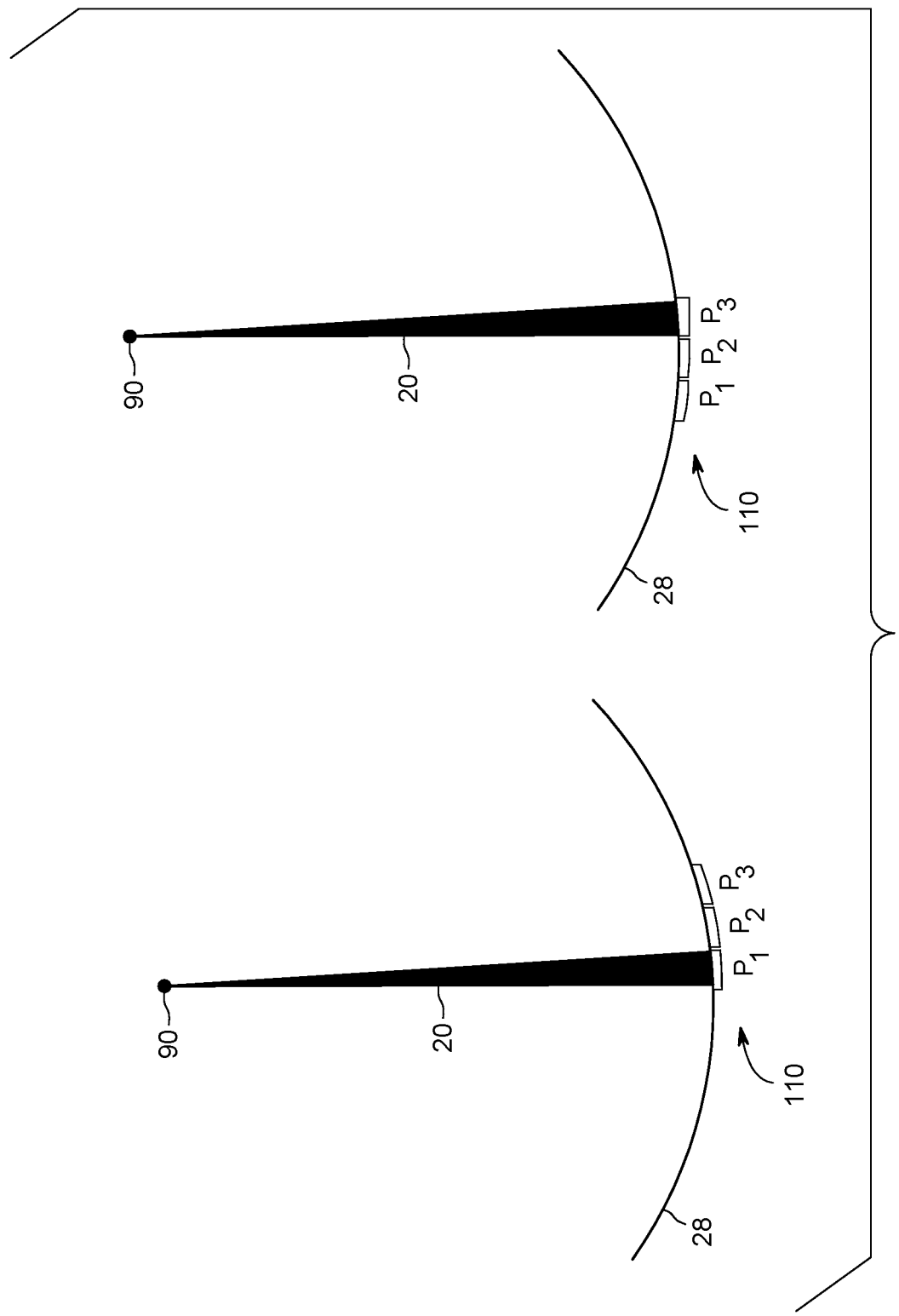
FIG. 6 depicts a source and detector arrangement at the beginning (left) and end (right) of a view, in accordance with aspects of the present disclosure.

To illustrate this issue and the detector signal summation approach, an example of a detector 28 upon which an X-ray beam 20 is incident is depicted in FIG. 6 at a first time and a subsequent time. In this example the focal spot 90 is frozen at a given point within the respective view, as described above. The detector 28 is composed of an array of pixel elements 110, three of which (P$_1$, P$_2$, P$_3$) are shown in the left and right examples.

At the first time, shown on the left, an X-ray beam 20 is shown emitted from the focal spot 90 and incident on a pixel, P$_1$, of detector 28 at the beginning of a respective view position. As shown at the second time on the right (corresponding to the rotation of the gantry supporting detector 28 and source 12 to the end of the respective view), the X-ray beam 20 is now incident on the detector at a different pixel, P$_3$. In the depicted example, the detector 28 has rotated, resulting in the changed incidence of the X-ray beam 20 with respect to pixels P$_1$, P$_2$, and P$_3$, during rotation, but the focal spot 90 is stationary in the absolute coordinate system due to the focal spot freezing discussed herein.

With this example in mind, at a given view a number of pixels (here three pixels P$_1$, P$_2$, and P$_3$) pass through the same location relative to the stationary or frozen X-ray beam 20. These pixels 110 all carry the same view information and may be summed together to get the entire view information. In one implementation, the present detector signal summation approach involves summing the signal detected at the detector 28 (i.e., at pixels 110) in a counter-rotational direction with respect to the signal acquisition for a given view.

The view information can be summed as illustrated in FIG. 7, which illustrates that the detected signals may be combined for a set of pixels P$_1$, P$_2$, and P$_3$ to ensure that the same X-ray in the absolute coordinate system corresponds to one measured value within a given view. For example, as noted above, the X-ray 20 that is illustrated in FIG. 6 is detected by P$_1$ at the beginning of the view (left most illustration) and by P$_3$ at the end of the view (rightmost illustration). Thus, the measurement corresponding to that X-ray 20 for the respective view is the combination of the detected signal of P$_1$, P$_2$, and P$_3$ sampled at a high frequency. For example, in one implementation each detector pixel 110 and its electronics has a sampling rate three times the view rate. The signal combination step can occur on the detector during data collection or with dedicated algorithm after data collection.

This approach may also be expressed mathematically, as shown in equation (1), where:

$$M_{i,j} = N_{i,j,1} + N_{i+1,j,2} + N_{i+2,j,3} \quad (1)$$

Thus, in this example, where each detector pixel 110 and its electronics has a sampling rate three times the view rate, for each view one detector pixel 110 samples three times the incoming X-ray signal, and produces three measurement signals $N_{i,j,k}$, where subscript i is pixel number, j is view number, and k=1, 2, 3. $M_{i,j}$ is, therefore, the combined sampled signal for a given view at a given detector pixel. Though this example relates a simplified scenario with respect to sampling rate, it should be appreciated that the sampling rate does not necessarily need to be an integral multiple of the number of pixels and can also be a fractional multiple value that is handled via interpolation.

Figure 8:
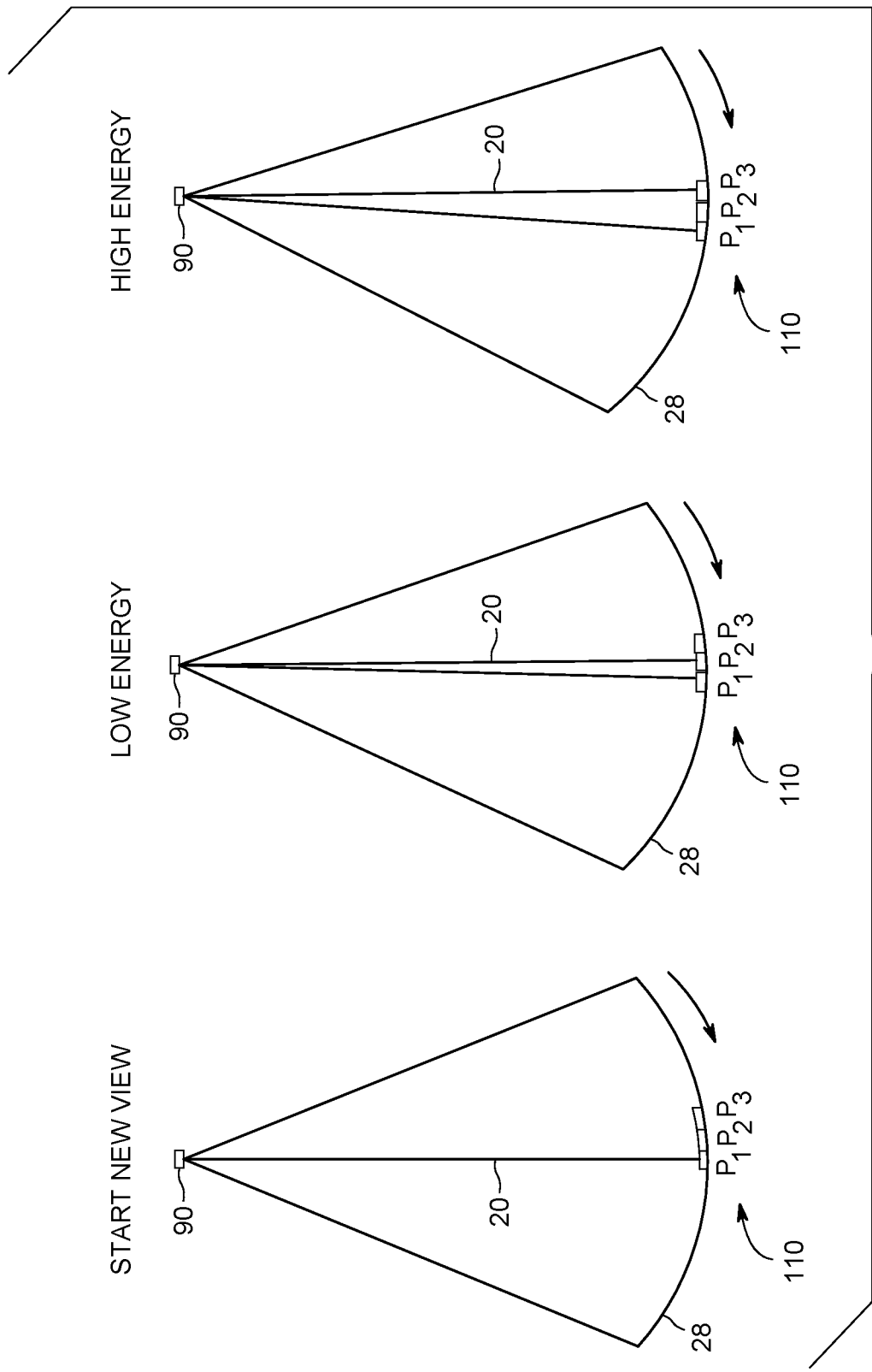
FIG. 8 depicts aspects of focal spot freezing and detector signal summation in a dual-energy context, in accordance with aspects of the present disclosure.

With the preceding in mind, one contemplated approach employs focal spot freezing (FSF) with detector signal summation (DSS) in a dual-energy context. For example, FSF and DSS techniques can be used together and applied to fast kV switching to freeze the projection view of both low and high energy emissions for that view, which eliminates the radial offset between the low- and high-energy projections, making it unnecessary to do view interpolation. For example, as shown in FIG. 8, the X-ray 20 emitted by a frozen focal spot 90 that passes the iso-center intersects with the detector pixel P$_1$ at the beginning of the view (left). The same X-ray 20 intersects with detector pixel P$_2$ and P$_3$ at the end of the low-energy view (middle) and high-energy view (right), respectively. The DSS approach recombines the measurements, ensuring that the signal generated by the same X-ray 20 (i.e. the one passing through the iso-center in this example) are summed up and assigned to the same detector pixel for both low- and high-energy, making the view registration unnecessary.

Figure 9:
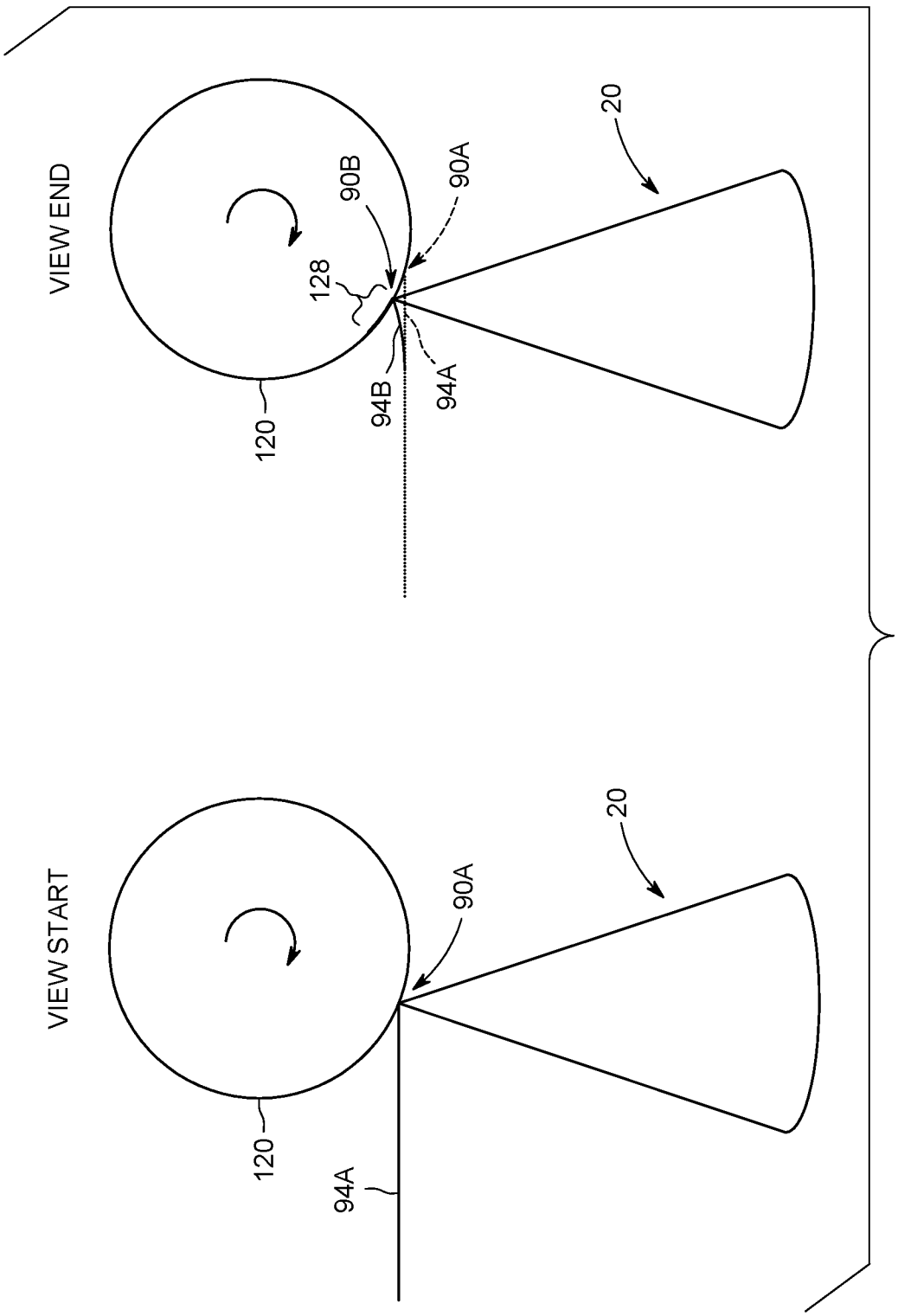
FIG. 9 depicts an example of a rotating target anode and adjusted electron beam at the beginning (left) and end (right) of a view in accordance with aspects of the present disclosure.

As may be appreciated from the present discussion, there may be power density considerations at the rotating target of the X-ray source 12 from which the X-rays are generated. For example, turning to FIG. 9, a schematic, top-down view of a rotating target 120 is shown using focal spot freezing at the start of a view (left) and at the end of the view (right). The electron beam 94 at both times is shown (electron beam 94A at the start of the view and electron beam 94B at the end of the view, with the electron beam 94A also shown at the end of the view for comparison). Correspondingly, focal spot 90 at both times is shown (focal spot 90A at the start of the view and focal spot 90B at the end of the view, with the focal spot 90A location also shown at the end of the view for comparison).

In a practical medical CT application, the target anode 120 is rotated at about 160 Hz. For a typical view rate of 0.5 ms, the target anode 120 rotates about 30° in the period of one view. Therefore, the focal spot 90 moves about 50 mm (shown by bracket 128) on the anode surface. With respect to the focal spot freezing operation, the focal spot 90 only need to move about 3 mm (the distance between focal spot 90A and 90B in the rightmost representation) on the anode surface to freeze the focal spot 90 in the patient coordinate system. In other words, the impact of focal spot freezing on tube power is equivalent to reducing the anode speed by about 6% in the described example (i.e., 3 mm/50 mm=~6%). This effective reduction in anode rotation speed may be compensated by increasing the anode rotation speed. After the view ends, the focal spot wobbles back from the end view location of the focal spot 90B to the location at the start of a view of the focal spot 90A. This has no impact on power density since the target anode 120 is not heated at the start of view location of the focal spot 90A. Thus, in one such embodiment, X-ray tube power is not affected if the target anode rotation is increased by about 6%. Such increases in target anode rotation speed are within the range possible using certain X-ray tube technologies, such as liquid bearings.

Technical effects of the invention include avoiding azimuthal blur in dual energy imaging with fast kV switching. In accordance with certain aspects, the focal spot position is frozen (i.e., held stationary in the patient coordinate system) within a view and the detector signals within the view are summed. This results in the low and high energy views within the signal being collected from the same position within the patient coordinate system. This eliminates the need for an interpolation and/or up-sampling step and improves the spatial resolution.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for acquiring computed tomography data, comprising:
continuously rotating an X-ray source and detector about an imaging volume during an examination, wherein the rotation of the X-ray source and detector is through a plurality of discrete view positions;
at each view position:
adjusting the focus of a beam of electrons on a target of the X-ray source so that a focal spot on the target remains relatively stationary relative to the imaging volume while in a respective view position; and
summing detector signals acquired over a plurality of pixels while in the respective view position;
processing the summed detector signals acquired at each view to reconstruct an image.

2. The method of claim 1, further comprising:
at each view position:
emitting X-rays at both a first X-ray energy spectrum and a second X-ray energy spectrum.

3. The method of claim 2, wherein no view interpolation step is performed to register the respective scan data associated with the first energy spectrum and the second X-ray energy spectrum for each view.

4. The method of claim 1, wherein adjusting the focus of the beam of electrons on the target comprises:
adjusting an electric/magnetic field within an X-ray tube so that the beam of electrons moves relative to the target to compensate for the gantry rotation.

5. The method of claim 1, wherein the sampling rate of the plurality of pixels is a function of the number of pixels that rotate through a respective view position during exposure of the view position.

6. The method of claim 1, wherein summing detector signals yields a combined sampled signal for each respective view position at a respective detector pixel.

7. The method of claim 6, wherein each combined sample signal is determined by adding multiple measurement signals based on at least their pixel number and view number.

8. A computed tomography (CT) imaging system, comprising:
a memory encoding processor-executable routines for holding a focal spot stationary and summing detector signal within each of a plurality of discrete view positions;
a processing component configured to access the memory and execute the processor-executable routines, wherein the routines, when executed by the processing component, cause the processing component to:
continuously rotate an X-ray source and detector of the CT imaging system about an imaging volume during an examination, wherein the rotation of the X-ray source and detector is through the plurality of discrete view positions;
at each view position:
adjust the focus of a beam of electrons on a target of the X-ray source so that a focal spot on the target remains relatively stationary relative to the imaging volume while in a respective view position; and
sum detector signals acquired over a plurality of pixels while in the respective view position;
process the summed detector signals acquired at each view to reconstruct an image.

9. The computed tomography (CT) imaging system of claim 8, wherein the routines, when executed by the processing component, cause the processing component to:
at each view position:
emit X-rays at both a first X-ray energy spectrum and a second X-ray energy spectrum.

10. The computed tomography (CT) imaging system of claim 9, wherein no view interpolation step is performed to register the respective scan data associated with the first energy spectrum and the second X-ray energy spectrum for each view.

11. The computed tomography (CT) imaging system of claim 8, wherein adjusting the focus of the beam of electrons on the target comprises:
adjusting an electric/magnetic field within an X-ray tube so that the beam of electrons moves relative to the target to compensate for the gantry rotation.

12. The computed tomography (CT) imaging system of claim 8, wherein the sampling rate of the plurality of pixels is a function of the number of pixels that rotate through a respective view position during exposure of the view position.

13. The computed tomography (CT) imaging system of claim 8, wherein summing detector signals yields a combined sampled signal for each respective view position at a respective detector pixel.

14. The computed tomography (CT) imaging system of claim 13, wherein each combined sample signal is determined by adding multiple measurement signals based on at least their pixel number and view number.

15. One or more non-transitory computer-readable media encoding processor-executable routines, wherein the routines, when executed by a processor, cause acts to be performed comprising:
continuously rotating an X-ray source and detector about an imaging volume during an examination, wherein the rotation of the X-ray source and detector is through a plurality of discrete view positions;
at each view position:
adjusting the focus of a beam of electrons on a target of the X-ray source so that a focal spot on the target remains relatively stationary relative to the imaging volume while in a respective view position; and
summing detector signals acquired over a plurality of pixels while in the respective view position;
processing the summed detector signals acquired at each view to reconstruct an image.

16. The one more non-transitory computer-readable media of claim 15, wherein the routines, when executed by the processor, cause further acts to be performed comprising:
at each view position:
emitting X-rays at both a first X-ray energy spectrum and a second X-ray energy spectrum.

17. The one more non-transitory computer-readable media of claim 15, wherein adjusting the focus of the beam of electrons on the target comprises:
adjusting an electric/magnetic field within an X-ray tube so that the beam of electrons moves relative to the target to compensate for the gantry rotation.

18. The one more non-transitory computer-readable media of claim 15, wherein the sampling rate of the plurality of pixels is a function of the number of pixels that rotate through a respective view position during exposure of the view position.

19. The one more non-transitory computer-readable media of claim 15, wherein summing detector signals yields a combined sampled signal for each respective view position at a respective detector pixel.

20. The one more non-transitory computer-readable media of claim 19, wherein each combined sample signal is determined by adding multiple measurement signals based on at least their pixel number and view number.

* * * * *